United States Patent [19]
Kawamura et al.

[11] Patent Number: 5,460,715
[45] Date of Patent: Oct. 24, 1995

[54] APPARATUS FOR FILTERING PLASMA

[75] Inventors: Akio Kawamura; Motoki Yonekawa, both of Sapporo; Eiji Sakashita; Hiroshi Kamogawa, both of Tokushima, all of Japan

[73] Assignee: Otsuka Pharmaceutical Factory, Inc., Naruto, Japan

[21] Appl. No.: 202,262

[22] Filed: Feb. 25, 1994

Related U.S. Application Data

[62] Division of Ser. No. 946,331, Nov. 10, 1992, Pat. No. 5,314,624.

[30] Foreign Application Priority Data

Mar. 26, 1991 [JP] Japan ................ 3-61747

[51] Int. Cl.⁶ ............... B01D 36/00; B01D 29/62
[52] U.S. Cl. ............. 210/97; 210/90; 210/108; 210/111; 210/130; 210/175; 210/195.1; 210/201; 210/202; 210/203; 210/252; 210/254; 210/295; 210/323.1; 210/333.01; 210/407; 210/409; 210/411; 210/420; 210/427; 210/436; 210/472; 604/4; 604/5; 604/6
[58] Field of Search ............. 210/90, 97, 333.01, 210/108, 111, 117, 120, 130, 143, 175, 195.1, 201, 202, 203, 252, 254, 295, 323.1, 407, 409, 411, 420, 427, 433.1, 436, 442, 446, 472, 321.69; 604/4, 5, 6

[56] References Cited

U.S. PATENT DOCUMENTS

| | | | |
|---|---|---|---|
| 4,350,156 | 9/1982 | Malchesky et al. | 210/434 |
| 4,834,888 | 5/1989 | Polaschegg | 210/646 |
| 4,963,253 | 10/1990 | Yen | 210/195.2 |

FOREIGN PATENT DOCUMENTS

| | | |
|---|---|---|
| 59-11865 | 1/1984 | Japan . |
| 59-129067 | 7/1984 | Japan . |
| 62-92836 | 6/1987 | Japan . |
| 63-127765 | 5/1988 | Japan . |
| 63-28626 | 6/1988 | Japan . |
| 1-34626 | 7/1989 | Japan . |

Primary Examiner—John Kim
Attorney, Agent, or Firm—Armstrong, Westerman, Hattori, McLeland and Naughton

[57] ABSTRACT

In a process for filtering plasma by separating blood into blood cells and plasma by a primary filter and filtering the separated plasma by a secondary filter to remove macromolecules from the plasma as harmful components, the loss of plasma to be discarded from the system by a procedure for eliminating plugging of the secondary filter can be diminished by opening an inner chamber of the secondary filter to the atmosphere to thereby lower the internal pressure of the chamber every time increase of the pressure to an upper limit value due to an increasing plugging tendency of the secondary filter is detected, and washing the interior of the secondary filter from the inner and outer chamber sides after the internal pressure has lowered.

14 Claims, 4 Drawing Sheets

APPARATUS FOR FILTERING PLASMA

This is a division of application Ser. No. 07/946,331, filed Nov. 10, 1992, now U.S. Pat. No. 5,314,624.

TECHNICAL FIELD

The present invention relates to a process for filtering plasma and an apparatus therefor, and more particularly to a method of regenerating a secondary filter by washing for use in the plasma filtration process, and to improvements in the apparatus for the process.

BACKGROUND ART

Various studies have revealed that macromolecules present in the blood of patients are pathogens of some kinds of diseases such as chronic articular rheumatism and systemic lupus erythematosus. Attempts are therefore made to treat such a disease and alleviate the symptoms by removing these macromolecules from the blood of the patient. Plasma filtration processes are used as means for this purpose.

The plasma filtration processes include a treatment for separating the blood collected from the patient into blood cells and plasma by a primary filter first, and a treatment for removing the harmful macromolecules from the plasma by a secondary filter to purify the plasma. The purified plasma from the secondary filter is mixed with the blood cells from the primary filter again, and the mixture is returned to the blood supply source (patient).

The plasma filtration processes are divided generally into two types according to the mechanism of filtering off the macromolecules by the secondary filter: one is a process wherein the substance to be removed is selected according to the pore size of the secondary filter (double filtration plasmapheresis), and the other is a process comprising cooling plasma to about 4° C. once to form a gel (so-called cryogel) containing the macromolecules which are the harmful components of plasma and separating off the gel with the secondary filter having relatively large pores (cryofiltration). The latter has the advantage that the harmful macromolecules can be reliably removed and therefore has attracted attention in recent years (see, for example, Examined Japanese Patent Publication HEI 1-34626).

The cryofiltration is almost similar to the double filtration plasmapheresis in mechanism with the exception of using means for cooling plasma and a secondary filter of different pore size. This process will be described with reference to FIG. 4. Blood is sent from a supply source to a primary filter 3 through a blood supply line 2 by the operation of a blood pump 1 and separated into blood cells and plasma. The separated blood cells are sent into a blood cell return line 4 so as to be mixed again with the purified plasma to be described below.

On the other hand, the plasma is sent by the operation of a plasma pump 5 through a plasma supply line 6 to a cooling coil portion 7 on the line 6 and then into a secondary filter 8, which filters the plasma. The plasma is cooled by the coil portion 7 usually to 4° C. to 25° C., preferably to about 4° C., whereby a cryogel of macromolecules is formed. The gel is filtered off from the plasma by the secondary filter. The filtrate from the secondary filter, i.e., purified plasma, is mixed again with the blood cells returned from the primary filter 3 while being returned through a purified plasma return line 9. The mixture is thereafter warmed to the original temperature by a heating bag 10 and returned to the supply source. In the drawing, indicated at 11 are dripping chambers, at 12 pressure sensors and at A a cooling zone.

With continued plasma filtration, however, the secondary filter 8 tends to become gradually plugged and therefore needs to be restored in function by eliminating the plugging.

The plugging is eliminated usually by methods employed in the double filtration plasmapheresis. These methods include:

(a) Replacement of the secondary filter.

(b) Washing of the interior of the secondary filter with physiological saline.

For example, Examined Japanese Patent Publication SHO 63-28626 discloses a method wherein two secondary filters are used as connected together in parallel, and one of the filters, when plugged, is changed over to the other. Further Unexamined Japanese Patent Publication SHO 59-129067 discloses a method wherein in the event of plugging, the internal pressure of inner chamber of the secondary filter is lowered to atmospheric pressure, and the filter is backwashed with a wash liquor supplied from the outer chamber side of the secondary filter.

With these methods (a) and (b), however, the whole amount, for example, about 200 to about 300 ml, of plasma remaining in the secondary filter is discarded by a single cycle of washing procedure. The secondary filter must be washed or replaced at least twice per cycle of plasma filtration operation, so that as much as 400 to 600 ml of plasma in total is to be discarded from the system. Consequently, the patient must be replenished with an albumin preparation and like expensive medicinal solutions, is economically burdened with an increased cost, suffers from deficiencies of substances which can not be replenished and is susceptible to side effects. Moreover, since the secondary filter is expensive, the method wherein more than one secondary filter is used results in a correspondingly increased treatment cost.

Especially with the cryofiltration wherein the secondary filter used has a relatively large pore size, the filtration efficiency is lowest at the start of filtration and gradually increases with accumulation of cryogel. Thus, this process has the problem that the filtration efficiency of the secondary filter markedly decreases every time the filter is replaced or washed.

DISCLOSURE OF THE INVENTION

An object of the present invention is to provide a plasma filtration process which is adapted to minimize the amount of plasma to be discarded from the system when the secondary filter is regenerated by washing, and an apparatus for the process.

Another object of the invention is to provide a plasma filtration process wherein the secondary filter can be regenerated by washing with a reduced amount of wash liquor in a shortened period of time, and an apparatus for the process.

Still another object of the invention is to provide a plasma filtration process wherein the secondary filter as regenerated by washing is usable to resume filtration of plasma with almost the same filtration efficiency as before regeneration, and an apparatus for the process.

Other features of the present invention will made apparent from the following description.

The present invention provides a process for filtering plasma by separating blood into blood cells and plasma by a primary filter, introducing the separated plasma into a secondary filter through a supply line, passing the plasma through the secondary filter from an inner chamber to an outer chamber to thereby filter off macromolecules from the plasma as harmful components and purify the plasma, and returning the purified plasma from the secondary filter through a return line while mixing the plasma with the separated blood cells from the primary filter into blood, the process being characterized in that the secondary filter is washed and regenerated by executing the pressure lowering procedure of opening the inner chamber of the secondary filter to the atmosphere every time increase of the internal pressure of the inner chamber to an upper limit value due to an increasing plugging tendency of the secondary filter is detected, and washing the interior of the secondary filter from the inner and outer chamber sides with a wash liquor after the internal pressure of the inner chamber has lowered while discharging the wash from the inner chamber to outside the system, the regeneration of the secondary filter being followed by a usual operation again.

According to the plasma filtration process of the invention, the inner chamber of the secondary filter is opened to the atmosphere upon the inlet-side pressure of the filter reaching the upper limit value, whereby the internal pressure of the inner chamber is lowered to atmospheric pressure.

The reduction of internal pressure of the secondary filter inner chamber produces a pressure difference between the inner and outer chambers of the filter to result in the tendency for the purified plasma in the outer chamber of higher pressure to flow backward toward the inner chamber of lower pressure. If the purified plasma return line is open in this case, a backflow tendency occurs also at the purified plasma return portion of the line toward its terminal end. To preclude the undesirable backflow at the return portion, the return line may be temporarily closed preferably at a portion thereof closer to the secondary filter before the inner chamber is opened to the atmosphere.

Owing to the tendency of backflow from the outer chamber of the secondary filter toward the inner chamber thereof, the filter medium separating the inner chamber from the outer chamber is backwashed preliminarily with the purified plasma which flows backward from the outer chamber toward the inner chamber.

Subsequent to the procedure for lowering the internal pressure of the inner chamber, a wash liquor is supplied to the outer chamber to start to backwash the filter medium, while the wash liquor is supplied also to the inner chamber, starting to wash the filter medium from the inner chamber side.

According to the invention, the secondary filter can be regenerated by preliminary backwashing with the purified plasma by virtue of a pressure difference between the inner and outer chambers and washing with the wash liquor from the inner and outer chamber sides, in a short period of time, for example, of about 10 seconds using the wash liquor in a reduced amount, for example, of about 20 to about 30 ml for the inner and outer chambers combined when the cooling temperature of the cooling zone is about 11° to about 18° C.

During the procedure for washing the secondary filter, plasma is discarded from the filter inner chamber to outside the system in an amount corresponding to the amount of wash liquor used, e.g., about 20 to about 30 ml.

The secondary filter contains usually about 200 to about 300 ml of plasma in the inner and outer chambers combined. With the present invention, the amount of plasma to be discarded from the system is, for example, 20 to 30 ml, which is only a very small portion of the whole amount, e.g., 200 to 300 ml, to be contained. The amount of plasma to be discarded can therefore be smaller than is the case with the conventional process wherein the whole amount is discarded from the system.

Since the secondary filter is regenerated by washing with a small amount of wash liquor in a short period of time, the plugging substances (cryogel) are not removed completely from the filter medium but partially remain thereon. Consequently, plasma filtration can be resumed with the secondary filter retaining its filtering ability without entailing a markedly reduced filtration efficiency that will occur when the filter is replaced by a new one.

According to the invention, the supply of plasma from the primary filter to the secondary filter may be continued or interrupted during the procedure for washing the secondary filter. When the supply of plasma is continued, the blood pump and plasma pump can be continuously driven during the washing procedure. This obviates the trouble of stopping these pumps every time the filter is washed. Further if the supply is continued, the whole amount of plasma supplied to the secondary filter during the washing procedure is discarded from the system, so that an increased amount of plasma is discarded from the system. The amount of increase, although varying with the time required for the washing procedure, is about 4 to about 6 ml as will be described later when the washing time is, for example, about 10 seconds. Such an increase poses no particular problem. The increase in the amount of plasma to be discarded can of course be eliminated by interrupting the supply of plasma to the secondary filter during the washing procedure.

To further diminish the loss of plasma due to disposal from the system during the procedure for washing the secondary filter, a plasma collecting procedure can be executed according to the invention after the internal pressure of inner chamber of the secondary filter has lowered and before the washing procedure is started.

The plasma collecting procedure is executed with the supply of plasma to the secondary filter interrupted and with the inner chamber held out of communication with the atmosphere, by supplying the wash liquor to the filter and forcing out the plasma in the secondary filter from the inner chamber into the purified plasma return line by way of the outer chamber in communication with the line as the wash liquor is supplied. This plasma collecting procedure is completed when the whole amount of plasma in the inner and outer chambers of the secondary filter has been replaced by the wash liquor, that is, when the wash liquor has been supplied in an amount corresponding to the capacity of the secondary filter. The completion of this procedure is followed by the foregoing procedure for washing the secondary filter.

The amount of wash liquor to be used for the secondary filter in this case may be increased to such an extent that the filtration efficiency of the secondary filter will not lower greatly, for example, to an extent approximately corresponding to the capacity of the secondary filter.

Although the plasma collecting procedure is executed with the secondary filter in a plugged state, the wash liquor which is, for example, physiological saline is less viscous than plasma and therefore readily passes through the filter.

During the plasma collecting procedure, the plasma may be recycled from the supply line to the return line via a bypass line parallel to the secondary filter without stopping the blood pump and plasma pump.

In the case where the plasma collecting procedure is executed, the inner and outer chambers of the secondary filter are filled with the wash liquor replacing the plasma, so that if the washing procedure is immediately followed by the usual operation, the whole amount of wash liquor in the inner and outer chambers will flow directly into the return line.

To reduce the amount of wash liquor flowing into the return line according to the invention, the wash liquor can be discharged from the system after the secondary filter has been washed and before the usual operation is resumed.

The wash liquor discharging procedure is executed with the inner chamber of the secondary filter opend to the atmosphere and with the return line closed, by supplying plasma to the filter inner chamber and discharging the wash liquor in the inner chamber from the system with the supply of plasma. This discharging procedure is completed when the whole amount of wash liquor in the inner chamber has been replaced by the plasma, and is followed by the usual operation. With the wash liquor thus discharged, the amount of wash liquor to be admitted to the return line when the usual operation is resumed is limited to an amount corresponding to the capacity of the filter outer chamber and is reduced by an amount corresponding to the capacity of the inner chamber.

BEST MODE OF CARRYING OUT THE INVENTION

The process of the invention for filtering plasma will be described below with reference to the accompanying drawings.

Figure 1:
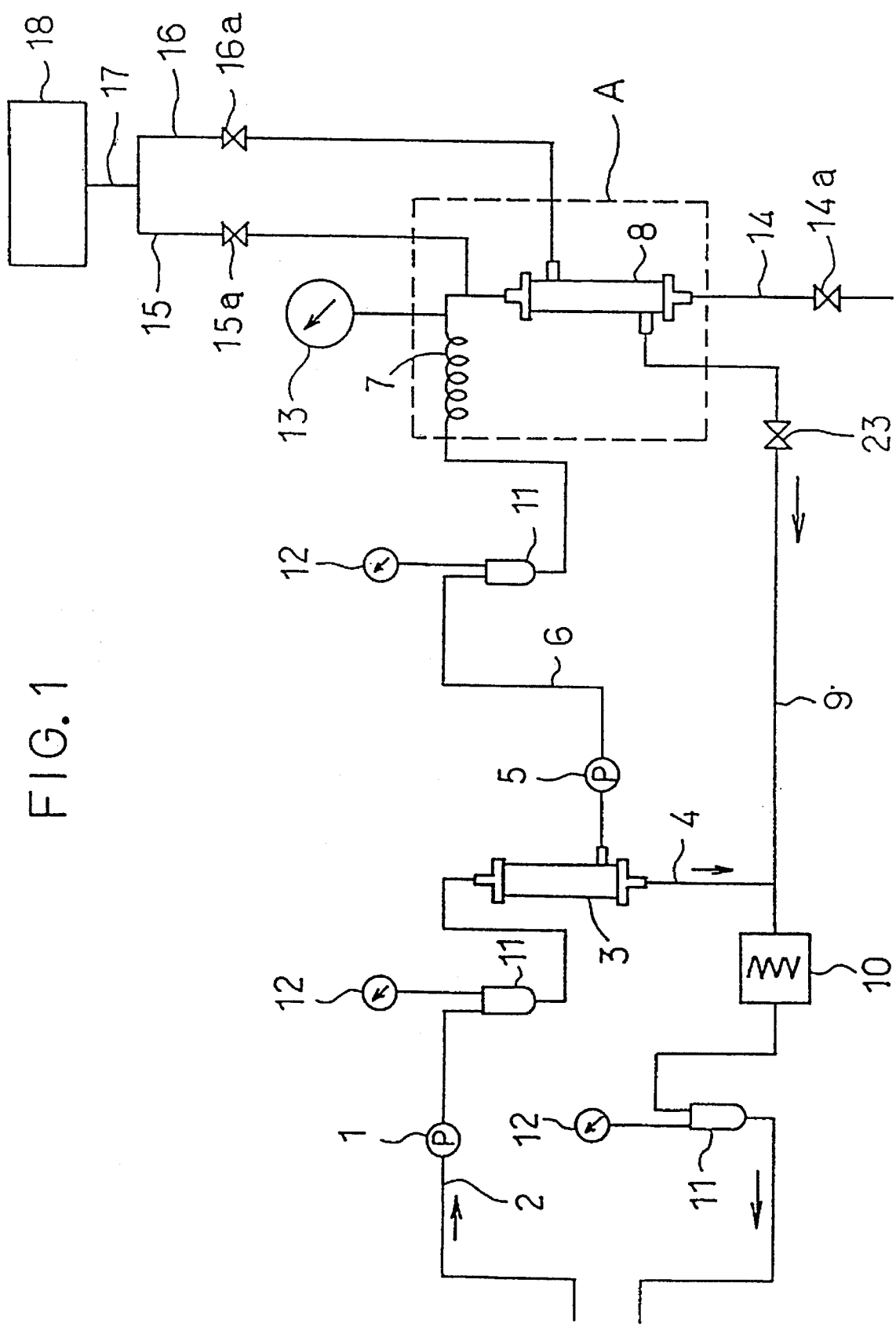
FIG. 1 is a flow chart showing an example of apparatus for use in practicing the plasma filtration process of the invention.
Figure 4:
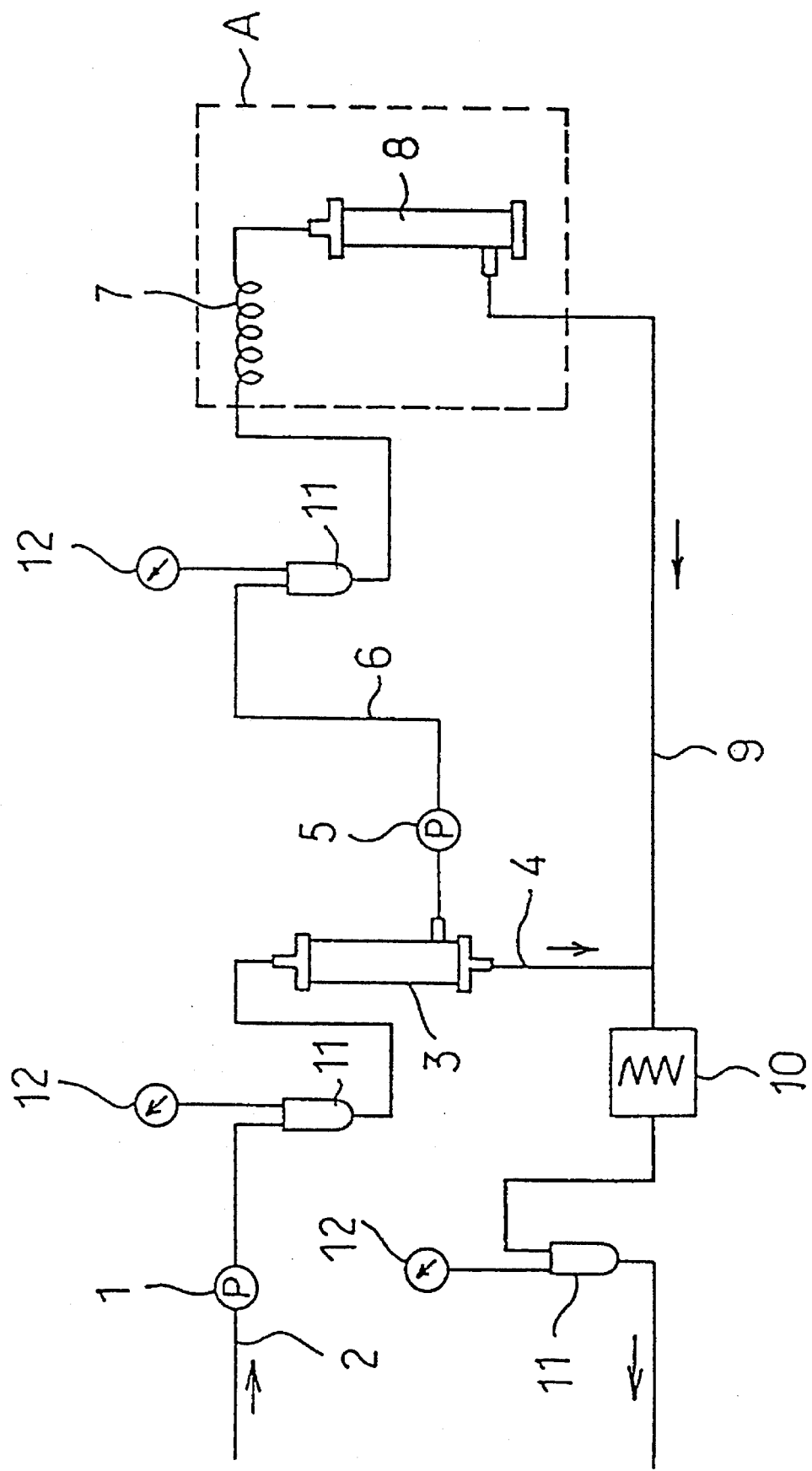
FIG. 4 is a flow chart for illustrating a conventional process.

FIG. 1 is a flow chart showing an example of apparatus for use in practicing the plasma filtration process of the invention. In FIGS. 1 and 4, like parts are designated by like reference numerals.

The apparatus of FIG. 1 for practicing the invention comprises, in addition to the construction of the conventional apparatus shown in FIG. 4, a pressure sensor 13 provided on the plasma supply line 6 close to the secondary filter 8, a waste line 14 equipped with a valve 14a and having one end connected to the lower end of the secondary filter 8 in communication with the inner chamber thereof and the other end opened to the atmosphere, a wash liquor supply line 15 equipped with a valve 15a and having one end connected to the plasma supply line 6 at a position upstream from the secondary filter 8 and the other end connected to a wash liquor supply source 18 via a common line 17, a wash liquor supply line 16 equipped with a valve 16a and having one end communicating with the outer chamber of the secondary filter 8 at a side wall upper portion thereof and the other end connected to the wash liquor supply source 18 through the common line 17, and a valve 23 mounted on the purified plasma return line 9 close to the secondary filter 8.

The pressure sensor 13 serves as means for detecting the increase of pressure at the inlet portion of the secondary filter 8 to an upper limit value due to an increasing plugging tendency, and also as means for detecting the decrease in the internal pressure of the inner chamber of the secondary filter 8 to a lower limit value. Instead of the sensor 13, the pressure sensor 12 provided for the dripping chamber 11 on the supply line 6 may be used for such pressure detection.

The waste line 14 having the valve 14a serves as means for lowering the internal pressure of the inner chamber by opening the chamber to the atmosphere and as means for discharging the wash from the inner chamber to outside the system.

The wash liquor supply lines 15, 16 having the valves 15a, 16a serve as means for washing the interior of the secondary filter from both sides of inner and outer chambers at the same time after the internal pressure of the inner chamber has dropped.

The valve 23 on the purified plasma return line 9 serves to hold the line 9 closed during the procedure for lowering the internal pressure of the secondary filter 8. The valve is held open during the usual operation.

Figure 2:
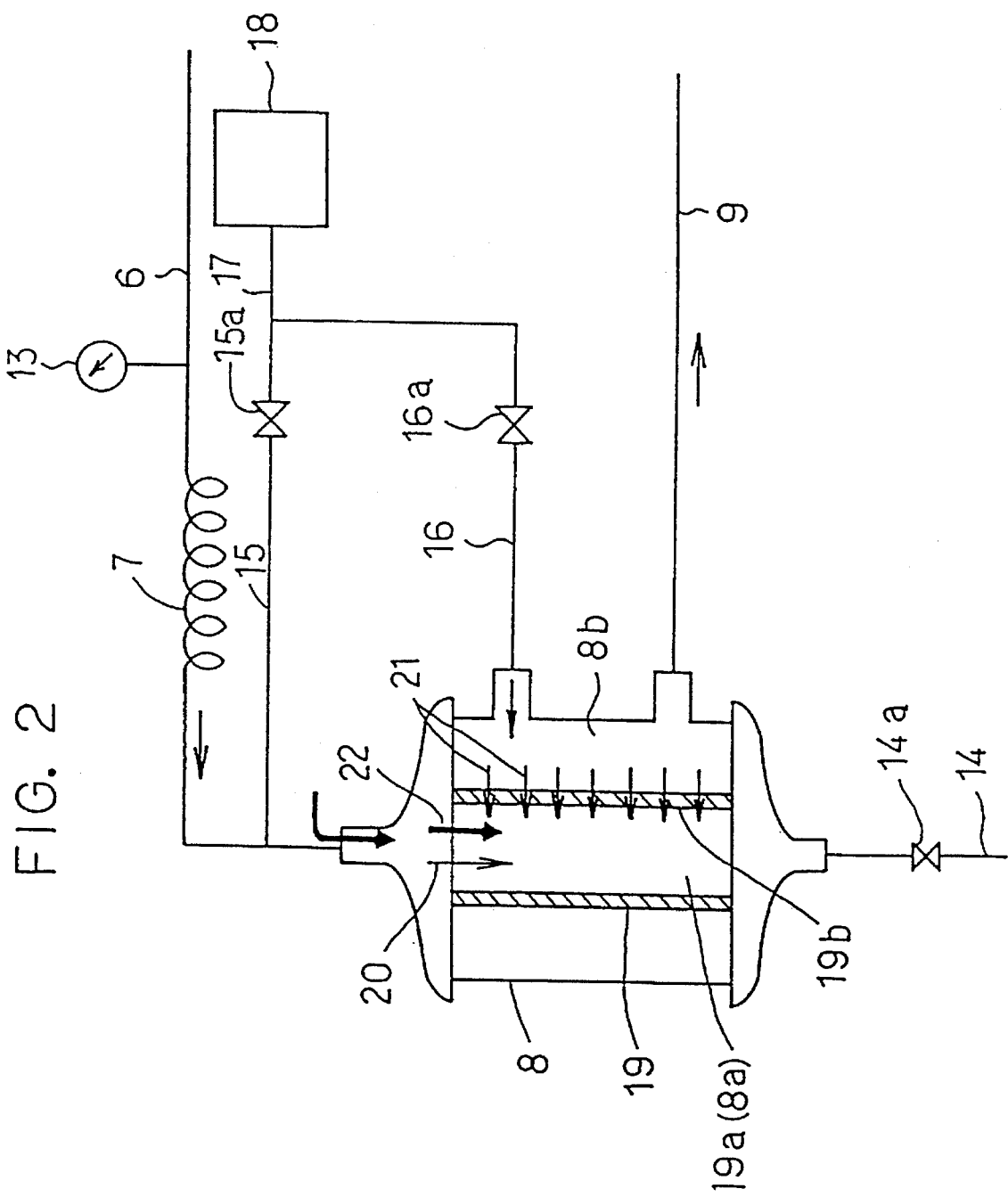
FIG. 2 is a diagram for illustrating the construction of a secondary filter in FIG. 1.

FIG. 2 is a diagram for illustrating the construction of the secondary filter 8. The secondary filter 8 has incorporated therein thousands of hollow fibers usually made of cellulose diacetate, polyvinyl alcohol, polyethylene, polypropylene, polysulfone, EVAL, PMMA (polymethyl methacrylate), PAN (polyacrylonitrile) or the like. For convenience sake, the filter medium is schematically represented by a single hollow fiber 19 shown as enlarged in the drawing. The pore size of the hollow fiber 19 is not limited specifically but is determined usually from the range of 0.01 to 0.5 micron in view of the degree to which plasma is cooled. Like the secondary filter, the primary filter 3 also comprises hollow fibers having such a pore size as to filter off blood cells. It is suitable that the pore size be about 0.2 to about 0.6 micron.

As indicated by a thin arrow 20 in FIG. 2, the plasma from the primary filter (see FIG. 1) flows through the plasma supply line 6 and the cooling coil portion 7 on the line 6 into the inner hollow space 19a of each hollow fiber 19 within the secondary filter 8, i.e., into an inner chamber 8a of the filter 8, usually at a rate of about 0.4 to about 0.6 ml/sec in total during the usual plasma filtration operation.

A gel of macromolecules, i.e. so-called cryogel, is formed in the plasma flowing into the hollow space 19a by cooling in the coil portion 7 and the secondary filter 8. When the plasma passes through the wall 19b of the fiber 19, the cryogel is captured by the wall 19b, and only the plasma component of blood passes through the wall 19b. The plasma purified by passing through the wall 19b flows from outside the wall 19b, i.e., from an outer chamber 8b of the secondary filter 8, toward the return line 9 connected thereto, as in the conventional process.

The cryogel captured by the wall 19b of the fiber 19 accumulates in the interior of the wall 19b and on the surface thereof defining the inner hollow space 19a with time. The accumulation gradually increases the internal pressure of the hollow space 19a of the fiber 19, i.e., of the filter inner chamber 8a, from the usual operating level of 0–20 mm Hg. The rise of pressure is detected by the sensor 13.

Upon the pressure detected by the sensor 13 reaching the upper limit value, e.g., about 300 mm Hg, the valve 14a on the waste line 14 opens from its closed state, consequently lowering the internal pressure of the hollow space 19a of the fiber 19, i.e., of the filter inner chamber 8a to atmospheric pressure. The pressure reduction produces a pressure difference between the hollow space 19a, i.e., the filter inner chamber 8a, inside the plugged wall 19b and the filter outer chamber 8b outside the wall, with the result that the purified plasma as treated and filling the outer chamber 8b tends to flow backward toward the inner chamber 8a. The wall 19b is therefore preliminarily backwashed owing to this backflow tendency.

If the backflow tendency of the purified plasma spreads toward the terminal end of the return line 9, a backflow of blood will occur at the purified blood return portion of the line 9 toward its terminal end. Such an undesirable backflow tendency of blood can be precluded by closing the valve 23 on the return line 9 from its open state before the valve 14a on the line 14 is opened.

The pressure reduction in the hollow space 19a, i.e., in the filter inner chamber 8a, is detected by the sensor 13. Simultaneously with or a short period of time after the pressure reduction, the valve 16a on the wash liquor supply line 16 communicating with the filter outer chamber 8b is opened from its closed state. Consequently, a wash liquor is supplied from its supply source 18 to the outer chamber 8b through the common line 17 and then through the supply line 16, for example, by driving a pump (not shown) or utilizing a head. The wall 19b is backwashed with the wash liquor thus supplied to the filter outer chamber 8b as indicated by arrows 21. The filter is backwashed with the wash liquor usually with the separated plasma continuously supplied to the secondary filter 8. The plasma sent into the secondary filter 8 via the line 6 during the backwashing is discharged from the system through the waste line 14, so that the backwashing must be accomplished rapidly within the shortest possible period of time. Further since the amount of plasma discharged from the inner hollow space 9a (or the inner chamber 8a) to outside the system through the waste line 14 during the backwashing approximately corresponds to the amount of wash liquor used, there arises a need to minimize the amount of wash liquor to be used.

Further in the cryofiltration, the filter achieves a higher filtration efficiency in the state in which some cryogel is present on the wall 19b than otherwise, so that use of an excess of wash liquor completely removes the cryogel from the wall 19b to result in a greatly reduced filtration efficiency. However, the wash liquor, when used in a decreased amount for backwashing, is unable to sufficiently wash away the cryogel as released by backwashing. Incidentally, untreated plasma always flows through the inner hollow space 19a at a total rate of 0.4 to 0.6 ml/sec, whereas the amount of plasma is too small to fully wash the cryogel away.

According to the present invention, therefore, the valve 15a on the wash liquor supply line 15 connected to the filter inner chamber 8a is opened from its closed state simultaneously when, or 2 to 3 seconds after, the valve 16a on the wash liquor supply line 16 for backwashing is opened, whereby during the backwashing, the wash liquor is supplied from the line 15 into the inner chamber 8a, i.e., into the inner hollow space 19a, in approximately the same amount as the backwashing liquor.

As indicated by a thick arrow 22 in FIG. 2, the wash liquor flowing into the hollow space 19a coacts with the untreated plasma flowing through the space 19a at all times, discharging the cryogel from the system via the waste line 14 while washing away the gel from the inner surface of the wall defining the space 19a.

According to the invention, plugging can be eliminated from the filter by preliminarily backwashing the filter with treated plasma by virtue of a pressure difference between the inner and outer chambers 8a, 8b and washing the filter with a wash liquor from the inner and outer chamber sides at the same time, in a short time, for example, of about 10 seconds using the wash liquor in a greatly diminished amount, e.g., about 20 ml in total.

After a predetermined period of washing procedure, the open valves 14a, 15a, 16a on the respective lines 14, 15, 16 are closed, while the closed valve 23 is opened to resume the usual filtration operation.

The procedure for eliminating plugging from the filter described is repeated based on the main indication of the pressure sensor 13. The plugging eliminating procedure is repeated empirically about four times per cycle of plasma filtration operation.

According to the invention, the amount of plasma discarded from the system per cycle of plugging eliminating procedure is about 20 ml corresponding to the total amount of wash liquor used plus 4 to 6 ml (0.4 to 0.6 ml×10 sec) of untreated plasma which is continuously sent forward, i.e., 24 to 26 ml in total, so that the corresponding amount for four repeated cycles is 96 to 104 ml. This amount is much smaller than 400 to 600 ml which is the corresponding amount of the conventional process. Thus, the amount of plasma to be discarded from the system can be reduced to about ⅕.

Even when the filter is washed with a smaller amount of wash liquor per cycle or for a shorter period of time per cycle than above, the same effect can be achieved by repeating the washing cycle more frequently. A slightly increased amount of wash liquor is usable per cycle when the washing cycle is repeated correspondingly less frequently.

While the secondary filter 8 is washed for regeneration, the supply of plasma to the filter may be continued or interrupted. When the supply of plasma to the secondary filter is continued as previously stated, the pumps 1 and 5 can be driven continuously during the washing regeneration procedure. This obviates the trouble of stopping the pumps 1 and 5 for every washing regeneration cycle. In the case where the supply of plasma is interrupted, on the other hand, no plasma is supplied to the secondary filter 8 during the washing procedure, so that the amount of plasma to be discarded can be diminished correspondingly.

To wash the secondary filter 2 for regeneration under automatic control, electromagnetic valves are usable as the valves 14a, 15a, 16a and 23 according to the invention. An exemplary mode of automatic control will be described briefly. When the pressure sensor 13 detects the rise of pressure to the upper limit value during the usual operation with the valves 14a, 15a and 16a closed and the valve 23 in the open state, the open valve 23 is closed and the closed valve 14a is opened in response to the resulting detection signal for pressure relief. When the sensor 13 detects the reduction of pressure to the lower limit value due to the pressure relief, the closed valves 15a, 16a are opened for the start of washing. A predetermined period of time thereafter, a timer or the like functions to close the open valves 14a, 15a and 16a and open the closed valve 23 to bring the system into usual operation.

Figure 3:
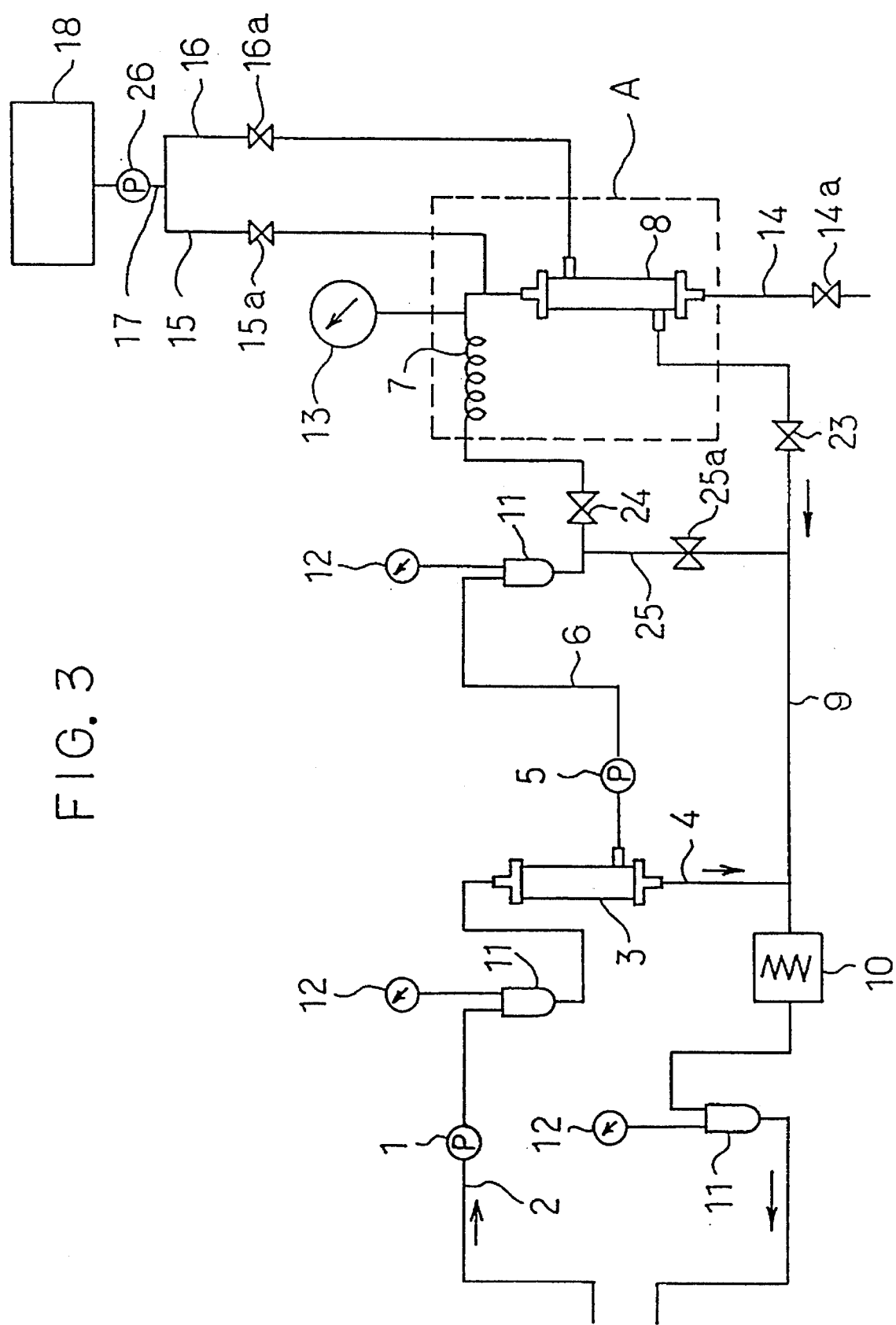
FIG. 3 is a flow chart showing another example of apparatus for use in practicing the plasma filtration process of the invention.

FIG. 3 shows another example of apparatus suitable for practicing the plasma filtration process of the invention.

The apparatus of the invention shown in FIG. 3 has plasma collecting means, wash liquor discharging means and untreated plasma recycling means in addition to the pressure relief means and washing means shown in FIG. 1.

The plasma collecting means serves to collect plasma from the inner and outer chambers of the secondary filter toward the return line 9 after pressure relief from the inner chamber of the filter 8 and before washing.

Of the wash liquor remaining in the inner and outer chambers after the secondary filter 8 has been washed and before the usual operation is resumed, the wash liquor in the inner chamber is discharged from the system by the wash liquor discharging means.

The untreated plasma recycling means serves to recycle plasma from the supply line to the return line while the supply of plasma to the secondary filter 8 is interrupted.

To provide these means, the apparatus shown in FIG. 3 has, in addition to the construction shown in FIG. 1, a valve 24 mounted on the plasma supply line 6, a wash liquor pump 26 mounted on the common line 17, and a bypass line 25 having a valve 25a and connecting a portion of the supply line 6 upstream from the valve 24 toward the primary filter 3 to the return line 9. Some components of these means are used in common.

Shown below is one cycle of the procedure for regenerating the secondary filter 8 by washing in practicing the plasma filtration process of the invention with use of the apparatus shown in FIG. 3.

Usual operation
↓
Detection of rise of inlet portion pressure of secondary filter 8 to upper limit value
↓
Pressure relief of inner chamber of secondary filter 8
↓
Detection of reduction in internal pressure of inner chamber to lower limit value
↓
Procedure for collecting plasma from inner and outer chambers of secondary filter 8
↓
Procedure for washing secondary filter 8
↓
Procedure for discharging wash liquor from inner chamber of secondary filter 8
↓
Usual operation The valves are opened or closed to the following positions during the procedures involved in one cycle shown above.
During usual operation
  Open position: valves 24, 23.
  Closed position: valves 14a, 25a, 15a, 16a
During pressure relief
  Open position: valves 24, 14a
  Closed position: valves 23, 25a, 15a, 16a
During plasma collecting procedure
  Open position: valves 23, 25a, 15a
  Closed position: valves 24, 14a, 16a
During washing procedure
  Open position: valves 25a, 15a, 16a, 14a
  Closed position: valves 24, 23
During wash liquor discharging procedure
  Open position: valves 24, 14a
  Closed position: valves 25a, 15a, 16a, 23

Among the above procedures, the pressure relief and washing procedures are substantially the same as in the case of FIG. 1.

The plasma collecting procedure and the wash liquor discharging procedure will be described below with reference to FIG. 3.

The plasma collecting procedure is executed with the supply of untreated plasam to the secondary filter 8 interrupted by closing the valve 24. To hold the pumps 1 and 5 in operation during the interruption, the bypass line 25 is opened, recycling the plasma through the channel of supply line 6 . bypass line 25 . return line 9.

On the other hand, the wash liquor is supplied from the line 15 to the inner chamber of the secondary filter 8 by the operation of the pump 26. As the wash liquor is supplied, the plasma in the inner and outer chambers is forced out from the outer chamber into the return line 9 communicating therewith and thereby collected.

Although the wash liquor is supplied to the inner chamber with the secondary filter 8 in a plugged state, the wash liquor passes through the plugged filter medium from the inner chamber to the outer chamber since the wash liquor is usually physiological saline and is less viscous than plasma.

Upon the pressure sensor 13 detecting the rise of pressure to the upper limit value during the supply of wash liquor to the inner chamber, the closed valve 14a is opened for pressure relief with the supply of wash liquor interrupted temporarily or without interrupting the supply.

The supply of wash liquor to the inner chamber is continued until the whole amount of plasma in the inner and outer chambers is replaced by the wash liquor. Since the capacity of the secondary filter 8 is known in advance, when the replacement is to be completed can be calculated, for example, from the flow rate measured by a flow meter (not shown) on the line 15. The completion of replacement is followed by the washing procedure as previously stated.

The loss of plasma to be discarded from the system during the washing procedure can be substantially eliminated by replacing the whole amount of plasma in the inner and outer chambers by the wash liquor and collecting the plasma toward the return line 9 before the washing procedure is started.

The liquid remaining in the inner and outer chambers of the secondary filter 8 after the washing procedure is substantially entirely the wash liquor because the plasma is wholly replaced by the wash liquor and collected from the inner and outer chambers before the washing procedure. Accordingly, the whole amount of wash liquor in the inner and outer chambers flows into the return line 9 when the usual operation is resumed immediately after the washing procedure.

Preferably, the amount of wash liquor to be admitted to the return line 9 is minimized. For this purpose, the wash liquor is discharged from the system sub to the washing procedure.

For the wash liquor discharging procedure, the valves 24, 14a are opened, and all the other valves are held closed. Consequently, the plasma flowing toward the bypass 25 during the plasma collecting procedure and the washing procedure flows into the inner chamber of the secondary filter 8 through the opened valve 24, while the wash liquor is discharged through the waste line 14 instead. The rate of supply of the plasma to the secondary filter 8 per second is known, so that after the whole amount of wash liquor in the inner chamber has been replaced by the plasma with the lapse of a specified period of time, the open valve 14a is closed and the closed valve 23 is opened, for example, by the action of a timer or the like to resume the usual operation.

Electromagnetic valves are usable as the valves of the apparatus shown in FIG. 3 as in the case of the apparatus of FIG. 1 so that the valves can be opened or closed under automatic control for various procedures.

We claim:

1. An apparatus for filtering plasma by separating blood into blood cells and plasma by a primary filter, introducing the separated plasma into a secondary filter through a supply line, passing the separated plasma through the secondary filter from an inner chamber to an outer chamber to thereby filter off macromolecules from the separated plasma as harmful components and produce a purified plasma, and returning the purified plasma from the secondary filter through a return line while mixing the purified plasma with the separated blood cells from the primary filter into blood, the apparatus comprising:

(i) a primary filter having an inlet for blood to be separated into blood cells and plasma and an outlet for separated plasma and an outlet for separated blood cells, (ii) a secondary filter having a plasma inlet connected to the outlet of the primary filter by a supply line, the secondary filter comprising an inner chamber having a plasma inlet connected to the supply line and an outer chamber having an outlet, (iii) a wash liquor inlet provided in the inner chamber of the secondary filter, (iv) a wash liquor inlet provided in the outer chamber of the secondary filter, (v) a return line from an outlet of the outer chamber of the secondary filter to said outlet of the primary filter for the separated blood cells, (vi) means for detecting an increase of the internal pressure of a plasma inlet portion of the secondary filter to an upper limit value, (vii) means for detecting a reduction of the internal pressure of the inner chamber to a lower limit value, (viii) means for opening the inner chamber to the atmosphere to lower the internal pressure of the inner chamber every time the pressure increase to the upper limit value is detected by the means for detecting increase of the internal pressure of the plasma inlet portion of the secondary filter, (ix) means for supplying a wash liquor to the secondary filter to both the wash liquor inlet of the inner chamber and the wash liquor inlet of the outer chamber every time the pressure reduction to the lower limit value is detected by the means for detecting reduction of the internal pressure of the inner chamber, and (x) a waste line connected to the inner chamber of the secondary filter for discharging the wash liquor to outside the apparatus while washing the secondary filter.

2. An apparatus for filtering plasma as defined in claim 1 which comprises means for replacing the plasma remaining in the inner and outer chambers of the secondary filter by the wash liquor and collecting the plasma toward the return line after the internal pressure of the inner chamber has lowered and before the secondary filter is washed.

3. An apparatus for filtering plasma as defined in claim 2 which comprises means for replacing the wash liquor in the secondary filter inner chamber by the plasma sent forward through the supply line and discharging the wash liquor from the apparatus after the secondary filter has been washed and before the usual operation is resumed.

4. An apparatus for filtering plasma as defined in claim 2 which comprises a bypass line for returning untreated plasma from the supply line directly to the return line while the supply of untreated plasma to the secondary filter is interrupted.

5. An apparatus for filtering plasma as defined in claim 1 wherein the return line for the purified plasma is provided with a valve which is closed when the internal pressure of the secondary filter inner chamber is lowered and which is opened when the usual operation is resumed.

6. An apparatus for filtering plasma as defined in claim 5 which comprises means for replacing the plasma remaining in the inner and outer chambers of the secondary filter by the wash liquor and collecting the plasma toward the return line after the internal pressure of the inner chamber has lowered and before the secondary filter is washed.

7. An apparatus for filtering plasma as defined in claim 6 which comprises means for replacing the wash liquor in the secondary filter inner chamber by the plasma sent forward through the supply line and discharging the wash liquor from the apparatus after the secondary filter has been washed and before the usual operation is resumed.

8. An apparatus for filtering plasma as defined in claim 6 which comprises a bypass line for returning untreated plasma from the supply line directly to the return line while the supply of untreated plasma to the secondary filter is interrupted.

9. An apparatus for filtering plasma as defined in claim 1 wherein a cooling zone is provided in the supply line so that the separated plasma is filtered in a cooled state by the secondary filter.

10. An apparatus for filtering plasma as defined in claim 9 which comprises a bypass line for returning untreated plasma from the supply line directly to the return line while the supply of untreated plasma to the secondary filter is interrupted.

11. An apparatus for filtering plasma as defined in claim 9 wherein the return line for the purified plasma is provided with a valve which is closed when the internal pressure of the secondary filter inner chamber is lowered and which is opened when the usual operation is resumed.

12. An apparatus for filtering plasma as defined in claim 11 which comprises means for replacing the plasma remaining in the inner and outer chambers of the secondary filter by the wash liquor and collecting the plasma toward the return line after the internal pressure of the inner chamber has lowered and before the secondary filter is washed.

13. An apparatus for filtering plasma as defined in claim 12 which comprises means for replacing the wash liquor in the secondary filter inner chamber by the plasma sent forward through the supply line and discharging the wash liquor from the apparatus after the secondary filter has been washed and before the usual operation is resumed.

14. An apparatus for filtering plasma as defined in claim 12 which comprises a bypass line for returning untreated plasma from the supply line directly to the return line while the supply of untreated plasma to the secondary filter is interrupted.

* * * * *